United States Patent [19]
Appleby et al.

[11] Patent Number: 5,872,289
[45] Date of Patent: Feb. 16, 1999

[54] HYDROLYSIS OF CARBOXYLIC ACID ALKYL ESTERS IN THE LIQUID PHASE

[75] Inventors: John Bruce Appleby, Perkiomenville; Francis Joseph Waller, Allentown; Stephen Charles Webb, Emmaus, all of Pa.

[73] Assignee: Air Products and Chemicals, Inc., Allentown, Pa.

[21] Appl. No.: 36,517

[22] Filed: Mar. 6, 1998

[51] Int. Cl.$^6$ ............ C07C 53/08; C07C 63/04; C07C 27/02
[52] U.S. Cl. ............ 562/607; 562/493; 568/877; 568/706; 568/735
[58] Field of Search .................. 562/607, 493; 568/877, 706, 735

[56] References Cited

U.S. PATENT DOCUMENTS

| | | |
|---|---|---|
| 1,647,676 | 11/1927 | Retze . |
| 2,866,820 | 12/1958 | Anselm et al. . |
| 2,936,321 | 5/1960 | Mercier .................. 260/541 |
| 4,016,180 | 4/1977 | Baierl .................. 260/247.9 |
| 5,502,248 | 3/1996 | Funk et al. .............. 562/606 |

FOREIGN PATENT DOCUMENTS 355104230  8/1998  Japan .

OTHER PUBLICATIONS

Izumi and coworkers (Catalysis Today, vol. 33, (1997) 371–409).

ACS Symposium on Carbon as . . . Support, Applied Catalysis A: General, vol. 142, No 1, N4–N5, Aug. 1996.

*Primary Examiner*—Gary Geist
*Assistant Examiner*—Rosalynd Keys
*Attorney, Agent, or Firm*—Keith D. Gourley

[57] ABSTRACT

A liquid-phase process for hydrolyzing a carboxylic acid alkyl ester having 2 to 18 carbon atoms to provide a product mixture comprising a carboxylic acid and an alcohol comprising contacting a feedstock comprising the carboxylic acid alkyl ester and water with an acidic carbon catalyst under reaction conditions sufficient to form the product mixture comprising the carboxylic acid and the alcohol. Suitable acidic carbon catalysts include charcoal and carbons produced from a variety of sources including coconut shells, coal, wood and peat. Carbon catalysts may be rendered acidic by treatment with nitric acid.

13 Claims, No Drawings

HYDROLYSIS OF CARBOXYLIC ACID ALKYL ESTERS IN THE LIQUID PHASE

BACKGROUND OF THE INVENTION

The hydrolysis of esters is limited by thermodynamic equilibrium, meaning that conversion of reactants to products is controlled by the ratio of the reactants, namely, the desired carboxylic acid alkyl ester, and water and reaction temperature. Conversion can be increased to some extent by increasing reaction temperature and/or by removing either of the reaction products, namely, the carboxylic acid or alcohol from the product mixture.

The hydrolysis of carboxylic acid methyl esters is a commercially significant reaction and is typically catalyzed by acid cation exchange resins. For example, U.S. Pat. No. 2,936,321 discloses a continuous process wherein an ester of a lower alkanoic acid such as methyl acetate is hydrolyzed in the presence of water and a catalyst consisting of a cation-exchange resin in its hydrogen form to produce a mixture of an acid (acetic acid), an alkanol (methanol), unreacted ester (methyl acetate), and water. The reaction mixture is withdrawn from the hydrolysis reactor and the ester is separated from the reaction mixture.

U.S. Pat. No. 5,502,248 discloses a continuous process for hydrolyzing carboxylic acid alkyl esters which utilizes a solid bed which acts as a catalyst for hydrolysis and as an adsorbent for at least one of the reaction products. The process is operated in simulated moving bed mode. A process embodiment is disclosed wherein the reactants are placed in contact with a strongly acidic macroreticular polymeric resin which functions as a hydrolysis catalyst and at least one solid which acts as an adsorbent for at least one hydrolysis product. Suitable adsorbents include molecular sieve carbon and activated carbon.

U.S. Pat. No. 4,016,180 discloses a low cost, two-stage adsorption-desorption process of concentrating dilute supplies of chemicals. The process is particularly adapted toward concentrating waste condensates derived from pulp-making operations such as the Kraft or sulfite processes, but may be applied toward treating all types of dilute organic or inorganic absorbable chemicals. The process comprises adsorbing a chemical fraction of the mixture to be concentrated onto activated carbon followed by regenerating the adsorbed chemicals and concentrating the same by fractional distillation whereupon the partially concentrated chemicals are again adsorbed, regenerated, subjected to a second fractional distillation concentration step, and recovered.

Example 1 of U.S. Pat. No. 4,016,180 discloses a process for concentrating the components of a waste liquor comprising methanol, furfural, acetic acid, sulfur dioxide and water. During the process, the initially adsorbed acetic acid is first substantially converted to methyl acetate during regeneration operations. Methyl acetate is not hydrolyzed to acetic acid when adsorbed onto the activated carbon adsorbent according to the Specification (col. 11, lines 60–68 and col. 12 lines 1–3) which states that "During the early stages of fractionation of course, the effluent leaving through line 112b can be recycled through line 148 or 149 in order to assure complete removal of the acetic acid from the system. It will be appreciated from the foregoing that in the operation of this embodiment there is no conversion of acetic acid to methyl acetate with consequent reconversion of the latter and accordingly the operation of the FIG. 2 is somewhat simpler."

Izumi and coworkers (Catalysis Today 33 (1997) 371–409) present a review of processes for hydrolyzing alkyl esters in the presence of solid acid catalysts. Only a few solid acid catalysts provide acceptable activity and stability for liquid phase hydrolysis of esters. Suitable solid acid catalysts include cation exchange resins such as Amberlyst 15, zeolites and cesium salts of 12-tungstophosphoric acid. These solid acid catalysts were tested for the hydrolysis of ethyl acetate at 60° C. using a mol ratio of ethyl acetate to water of 38.8 to 1.

Researchers are searching for carboxylic acid alkyl ester hydrolysis catalysts which can be operated at higher temperatures than conventional hydrolysis catalysts in order to maximize conversion to the desired products of the corresponding carboxylic acid and alcohol while minimizing formation of undesirable byproducts such as dialkyl ethers which are difficult to separate from the product mixture.

BRIEF SUMMARY OF THE INVENTION

The present invention relates to a liquid-phase process for hydrolyzing a carboxylic acid alkyl ester having 2 to 18 carbon atoms to provide a product mixture comprising a carboxylic acid and an alcohol. The process comprises contacting a feedstock including the carboxylic acid alkyl ester and water with an acidic carbon catalyst under reaction conditions sufficient to form the product mixture comprising the carboxylic acid and the alcohol.

More preferably, the present invention relates to a liquid-phase process for hydrolyzing a carboxylic acid methyl ester represented by the formula $RCO_2CH_3$ wherein R represents a hydrogen atom or a linear or branched alkyl having from 1 to 16 carbon atoms to provide a product mixture comprising a carboxylic acid and methanol comprising contacting a feedstock comprising the carboxylic acid methyl ester and water with an acidic carbon catalyst under reaction conditions sufficient to provide the product mixture comprising the carboxylic acid and methanol.

Preferred carboxylic acid alkyl esters to be utilized in the process feedstock are represented by

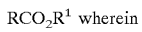

$RCO_2R^1$ wherein

Formula 1

R represents a hydrogen atom, a linear or branched alkyl having from 1 to 16 carbon atoms, phenyl, alkyl-substituted phenyl, naphthyl, or alkyl-substituted naphthyl and $R^1$ represents a linear or branched alkyl having from 1 to 17 carbon atoms, phenyl, alkyl-substituted phenyl, naphthyl, or alkyl-substituted naphthyl.

Representative examples of suitable carboxylic acid alkyl esters include methyl acetate, ethyl acetate, propyl acetate, butyl acetate, 2-butyl acetate, methyl formate, ethyl formate, 2-butyl formate, methyl propionate, ethyl propionate, propyl propionate and butyl propionate.

The carboxylic acids formed from the subject process will depend upon the particular carboxylic acid alkyl ester to be hydrolyzed as represented in Formula 1. However, the carboxylic acids formed from the subject process are represented by the following formula:

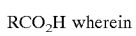

$RCO_2H$ wherein

Formula 2

R represents a hydrogen atom, a linear or branched alkyl having from 1 to 16 carbon atoms, phenyl, alkyl-substituted phenyl, naphthyl, or alkyl-substituted naphthyl.

The phrase, linear or branched alkyl means that the alkyl functionality may consist of a primary, secondary or tertiary alkyl.

Carboxylic acids capable of being produced according to the present process include, but are not limited to methanoic acid, ethanoic acid, propanoic acid, butanoic acid, pentanoic acid, hexanoic acid, heptanoic acid, octanoic acid, nonanoic acid, decanoic acid, undecanoic acid, dodecanoic acid, tridecanoic acid, tetradeconoic acid, and pentadeconoic acid and branched carboxylic acids such as 1-propanoic acid, 2-propanoic acid, 1-butanoic acid, 2-butanoic acid, 2-methyl-2-propanoic acid, 2-methyl-1-propanoic acid, 2-ethyl-1-hexanoic acid, benzenecarboxylic acid, 2-methylbenzenecarboxylic acid, 3-methylbenzenecarboxylic acid and 4-methylbenzenecarboxylic acid.

The alcohols formed from the subject process will depend upon the particular carboxylic acid alkyl ester to be hydrolyzed as represented in Formula 1. However, the alcohols formed from the subject process are represented by the following formula:

$$R^1-OH$$

Formula 3 wherein $R^1$ represents a linear or branched alkyl having from 1 to 17 carbon atoms, phenyl, alkyl-substituted phenyl, naphthyl, or alkyl-substituted naphthyl. The phrase, linear or branched, means that the alkyl functionality of the alcohol may consist of a primary, secondary or tertiary alkyl. Thus, alcohols capable of being produced according to the present process include but are not limited to methanol, ethanol, propanol, butanol, pentanol, hexanol, heptanol, octanol, nonanol, decanol, undecanol, dodecanol, tridecanol, tetradeconal, pentadecanol and branched alcohols such as 1-propanol, 2-propanol, 1-butanol, 2-butanol, 2-methyl-2-propanol, 2-methyl-1-propanol, and 2-ethyl-1-hexanol.

Typical reaction conditions sufficient to convert the feedstocks of the present process to the desired products include a temperature ranging from 40° C. to 200° C., and preferably from 60° C. to 200° C. The reactor pressure is controlled as a function of temperature in order to retain the reactants in the liquid phase. Reactor pressure typically does not exceed about 700 psia. Any conventional batch reactor or continuous flow reactor can be employed to operate the process of the present invention.

The carbon catalysts of the present invention are materials of poorly developed crystallinity and include but are not limited to charcoal and carbons produced from a variety of sources including coconut shells, coal, wood and peat. The carbon catalysts of the present invention are rendered acidic by conventional oxidation treatments such as surface oxidation treatments in oxygen, oxidizing solutions such as potassium persulfate, nitrate, iodate, aqueous chlorine and hydrogen peroxide. Preferably, the carbon catalysts are rendered acidic by oxidation with nitric acid.

The desired products, namely the carboxylic acid and alcohol, can be conveniently separated from the product mixture containing unreacted carboxylic acid alkyl ester and water by conventional techniques such as distillation.

BRIEF DESCRIPTION OF SEVERAL VIEWS OF THE DRAWINGS

NONE

DETAILED DESCRIPTION OF THE INVENTION

The present invention relates to a liquid phase process for hydrolyzing carboxylic acid alkyl esters in the presence of acidic carbon catalysts to form the corresponding carboxylic acid and alcohol. The acidic carbon catalysts of this process provide significant improvements over prior art catalysts. As shall be discussed in greater detail, processes for hydrolyzing carboxylic acid alkyl esters which employ acidic carbon catalysts can be operated at higher temperatures than corresponding hydrolysis processes which utilize most conventional catalysts thereby providing improved conversion to the desired products. The catalysts of the claimed process produce essentially no dialkyl ether byproducts which eliminates costly separation steps typically required in prior art processes wherein such unwanted ether byproducts must be separated from the desired products. Moreover, conversion to the desired products is increased because essentially no reactants are converted to unwanted ether byproducts.

The subject invention may be successfully utilized to hydrolyze at least one carboxylic acid alkyl ester to form at least one alcohol and at least one carboxylic acid. The most general embodiment of the invention relates to a liquid-phase process for hydrolyzing a carboxylic acid alkyl ester having 2 to 18 carbon atoms to provide a product mixture comprising a carboxylic acid and an alcohol. The process comprises the steps of contacting a feedstock comprising the carboxylic acid alkyl ester and water with an acidic carbon catalyst under reaction conditions sufficient to form the product mixture comprising the carboxylic acid and the alcohol. The respective components of the product mixture may be separated from the product mixture or the product mixture may be utilized as a feedstock in an alternate process.

Suitable feedstocks for use in the hydrolysis process include at least one carboxylic acid alkyl ester containing from 2 to 18 carbon atoms and water. The amount of water is typically controlled in order to reduce costs associated with separating unreacted water from the product mixture. However, additional amounts of water may be utilized in the process when the catalyst shows reduced activity due to catalyst aging or deactivation. Generally, the mol ratio of water to carboxylic acid alkyl ester ranges from 1/1 to about 10/1 and preferably ranges from 1/1 to 5/1. The process may be operated using a feedstock having a mol ratio of water to carboxylic acid alkyl ester of less than 1/1 although such a mol ratio would disrupt the process equilibrium resulting in reducing conversion to the desired products.

The feedstock desirably constitutes a single phase wherein the water is miscible in the carboxylic acid alkyl ester. As the molecular weight of the carboxylic acid alkyl ester increases, its miscibility in water tends to decrease. Miscibility can be improved by adding the carboxylic acid and/or alcohol to be produced into the feedstock in an amount sufficient to render miscible the carboxylic acid alkyl ester and water.

As previously stated, the acidic carbon catalysts of the present invention are capable of withstanding higher temperatures than conventional hydrolysis catalysts. One of ordinary skill in the art shall recognize that conversion to product can increase with increasing reaction temperature in equilibrium limited processes. Thus, the feedstock to be utilized in the present process may be the product mixture obtained from a conventional process for converting carboxylic acid alkyl esters to the corresponding carboxylic acid and alcohol which employs known catalysts such as ion exchange resins. Conversion of reactants to the desired products is further increased because the process temperature employed in the claimed process may be higher than the temperature employed in the conventional process thereby providing increased conversion to the desired products.

Typical reaction conditions sufficient to convert the feedstocks of the present process to the desired products include a temperature ranging from 40° C. to 200° C., and preferably from 60° C. to 200° C. The reactor pressure is controlled as a function of temperature in order to retain the reactants in the liquid phase. Reactor pressure typically does not exceed about 700 psia. Any conventional batch reactor or continuous flow reactor can be employed to operate the process of the present invention.

In the case wherein the desired products are produced utilizing a two-step process wherein the first step comprises a hydrolysis reaction which employs conventional catalysts and the second step comprises a hydrolysis reaction which employs Applicants' acidic carbon catalysts to further convert the reactants present in the product mixture obtained in the first step, the temperature employed in the second step is typically higher than the temperature employed in the first step. The carbon catalysts can be operated at a temperature up to about 200° C. using a typical feedstock of the carboxylic acid methyl ester and water presently used in existing hydrolysis processes.

An example of a two-step hydrolysis process is the reaction of methyl acetate with water in the presence of a conventional hydrolysis catalyst operated at a given temperature, for example, 100° C., to produce a feedstock containing acetic acid and methanol and unreacted methyl acetate and water. This feedstock is introduced into a second reactor containing the acidic carbon catalysts of the present invention operated at a temperature typically greater than the temperature employed in the first reactor, for example, 150° C., in order to further convert unreacted methyl acetate and water to acetic acid and methanol. The present invention allows the equilibrium concentration at 150° C. to be obtained without the formation of dimethyl ether which typically occurs from the dehydration of methanol when conventional hydrolysis catalysts are employed.

Preferred carboxylic acid alkyl esters to be utilized in the process feedstock are represented by $RCO2R^1$ wherein Formula 1

R represents a hydrogen atom, a linear or branched alkyl having from 1 to 16 carbon atoms, phenyl, alkyl-substituted phenyl, naphthyl, or alkyl-substituted naphthyl and $R^1$ represents a linear or branched alkyl having from 1 to 17 carbon atoms, phenyl, alkyl-substituted phenyl, naphthyl, or alkyl-substituted naphthyl.

Representative examples of suitable carboxylic acid alkyl esters include methyl acetate, ethyl acetate, propyl acetate, butyl acetate, 2-butyl acetate, methyl formate, ethyl formate, 2-butyl formate, methyl propionate, ethyl propionate, propyl propionate and butyl propionate.

The particular carboxylic acid to be formed from the subject process will depend upon the carboxylic acid alkyl ester to be hydrolyzed as represented in Formula 1. However, the carboxylic acids formed from the subject process are represented by the following formula:

$RCO_2H$ wherein

Formula 2

R represents a hydrogen atom, a linear or branched alkyl having from 1 to 16 carbon atoms, phenyl, alkyl-substituted phenyl, naphthyl, or alkyl-substituted naphthyl. The phrase, linear or branched alkyl means that the alkyl functionality may consist of a primary, secondary or tertiary alkyl.

Carboxylic acids capable of being produced according to the present process include, but are not limited to methanoic acid, ethanoic acid, propanoic acid, butanoic acid, pentanoic acid, hexanoic acid, heptanoic acid, octanoic acid, nonanoic acid, decanoic acid, undecanoic acid, dodecanoic acid, tridecanoic acid, tetradeconoic acid, and pentadeconoic acid and branched carboxylic acids such as 1-propanoic acid, 2-propanoic acid, 1-butanoic acid, 2-butanoic acid, 2-methyl-2-propanoic acid, 2-methyl-1-propanoic acid, 2-ethyl-1-hexanoic acid, benzenecarboxylic acid, 2-methylbenzenecarboxylic acid, 3-methylbenzenecarboxylic acid and 4-methylbenzenecarboxylic acid.

The alcohols capable of being produced according to the present process will depend upon the particular carboxylic acid alkyl ester to be hydrolyzed as represented in Formula 1. However, the alcohols formed from the subject process are represented by the following formula:

$R^1$—OH

Formula 3 wherein $R^1$ represents a linear or branched alkyl having from 1 to 17 carbon atoms, phenyl, alkyl-substituted phenyl, naphthyl, or alkyl-substituted naphthyl. The phrase, linear or branched, means that the alkyl functionality of the alcohol may consist of a primary, secondary or tertiary alkyl.

Alcohols capable of being produced according to the present process include but are not limited to methanol, ethanol, propanol, butanol, pentanol, hexanol, heptanol, octanol, nonanol, decanol, undecanol, dodecanol, tridecanol, tetradeconal, pentadecanol and branched alcohols such as 1-propanol, 2-propanol, 1-butanol, 2-butanol, 2-methyl-2-propanol, 2-methyl-1-propanol, and 2-ethyl-1-hexanol.

By way of example, if the desired alcohol product is methanol (wherein $R^1$ is $CH_3$), then the carboxylic acid alkyl ester to be utilized in the feedstock for reaction according to the present process possesses the formula $RCO_2CH_3$ wherein R is defined as previously described according to Formula 1. If the desired carboxylic acid product is acetic acid (R is $CH_3$), then the carboxylic acid alkyl ester to be utilized in the feedstock for reaction according to the present process possesses the formula $CH_3CO_2R'$ wherein R' is defined as previously described.

The desired products, namely the carboxylic acid and alcohol, can be conveniently separated from the product mixture containing unreacted carboxylic acid alkyl ester and water by conventional techniques such as distillation and the like.

The catalysts according to the present invention are acidic carbon catalysts. Acidic carbons are defined as those carbons that show acidic behavior and adsorb appreciable amounts of bases but very little of acids. The term, appreciable, means an amount of base which is sufficient to identify the carbon as having an acidic character. Suitable acidic carbon catalysts may generally be obtained when carbons are outgassed at high temperatures in vacuum or in inert atmosphere in the presence of oxygen at temperatures ranging from 200° to 700° C. Suitable acidic carbon catalysts can also be produced by oxidizing as-received carbons with oxidants in gaseous or solution phase. The optimum temperature for the development of maximum capacity to adsorb bases has been found to be around 400° C.

One of ordinary skill in the art shall recognize that carbon is known to possess either an acidic or basic character. Carbon is known to exist in nature in well-defined crystalline forms such as diamond and graphite or in forms exhibiting poorly developed crystallinity such as charcoal, coke, carbon black to name a few. The carbon catalysts of the present invention are materials of poorly developed crystallinity and include but are not limited to charcoal and carbons produced from a variety of sources including coconut shells, coal, wood and peat.

The carbon catalysts of the present invention are rendered acidic by conventional oxidation treatments such as surface oxidation treatments in oxygen, oxidizing solutions such as potassium persulfate, nitrate, iodate, aqueous chlorine and hydrogen peroxide. Preferably, the carbon catalysts are rendered acidic by oxidation with nitric acid. Such treatments are believed to result in the fixation of considerable amounts of oxygen functionality on the carbon. These types of oxygen functionality are strongly acidic groups postulated as $CO_2H$ groups, lactones, and weakly acid groups postulated as phenols, and carbonyls. Oxidation by nitric acid or hydrogen peroxide for short periods of time enhances the strong and weak acid groups whereas longer oxidation time is believed to enhance only weak acid structures.

The acidic carbon catalysts can be prepared by subjecting any carbon with nitric acid to provide a weight loss of about 25–30%, resulting in the fixation of considerable amounts of oxygen, most of which is desorbed as $CO_2$ on evacuation. The base neutralization capacity of the oxidized carbon increased in each case in proportion to the amount of $CO_2$ complex formed.

The following examples are not intended to limit the scope of the present invention, but are merely illustrative of the hydrolysis of representative carboxylic acid alkyl esters utilizing acidic carbon catalysts.

EXPERIMENTAL

Applicants tested their liquid phase process for hydrolyzing carboxylic acid alkyl esters in the presence of acidic carbon catalysts using a conventional packed bed reactor consisting of a reactor tube having a 0.5" outer diameter and a 0.049" wall. A single phase liquid feedstock containing the desired carboxylic acid alkyl ester and water was pumped through the packed bed reactor containing the enumerated hydrolysis catalyst. Pressure sufficient to retain the system in liquid state was maintained using a conventional back-pressure regulator. The product mixture obtained after running the process was subjected to a refrigerated bath in order to collect the product mixture as a liquid. Product mixtures for each run were analyzed on a HP 5890 Gas Chromatograph. The composition of the product mixture was determined using a flame-ionization detector, while water was detected by a thermal conductivity method.

Examples 1 and 2 present general procedures for preparing acidic carbon catalysts which are suitable for use in the claimed process.

EXAMPLE 1

GENERAL PROCEDURE FOR PREPARING AN ACIDIC CARBON CATALYST 5 grams of a desired carbon catalyst is placed in a 250 ml beaker. Concentrated $HNO_3$ (25 ml) is slowly added to the catalyst. The catalyst is then allowed to set for about 15 minutes. The beaker is placed on a hot plate and its contents are gently boiled to dryness at 80° to 100° C. for about one hour to yield an acidic carbon catalyst. Optionally, 0.4M Cu(ll) acetate solution (25 ml) may be added following the $HNO_3$ and before boiling. The acidic carbon catalyst is then washed with distilled water to neutral pH and dried at 110° C. for 12 hours.

EXAMPLE 2

ALTERNATE GENERAL PROCEDURE FOR PREPARING AN ACIDIC CARBON CATALYST

The general procedure of Example 1 is followed except that nitric acid is not boiled to dryness. 5 grams of a desired carbon catalyst is placed in a 250 ml beaker. Concentrated $HNO_3$(25 ml) is slowly added to the carbon. The carbon is allowed to set for approx. 15 minutes. The carbon is rinsed with distilled water to neutral pH and dried at 110° C. for 12 hours.

Examples 3–5 illustrate the inherent problem of dimethyl ether (DME) formation which occurs when methyl acetate is hydrolyzed in the presence of conventional ion-exchange resins. DME is formed at reaction temperatures of 95° C., 100° C. and 150° C., respectively.

EXAMPLE 3 (COMPARATIVE)

HYDROLYSIS OF METHYL ACETATE OVER AMBERLYST 131 CATALYST AT 100° C.

Amberlyst 131 ion-exchange resin (Rohm & Haas) was dried at 110° C. for 12 hours. Two grams of this resin were loaded in a reactor tube to form a catalyst bed. A feedstock of water, methyl acetate, methanol, and acetic acid having mole fractions 0.633, 0.300, 0.033, and 0.034 respectively. This feedstock represents a 10 percent hydrolyzed methyl acetate/water feedstock. The feedstock was pumped through the catalyst bed. Pressure was maintained at 100 psig and temperature was maintained at 100° C. Residence time through the catalyst bed was varied by varying the pumping rate. The catalyst bed was allowed to purge for a minimum of eight hours. Each sample was collected for a minimum of twelve hours. Each sample was then analyzed by gas chromatography to determine composition. Conversion was calculated based upon acetic acid and methanol. The following results were obtained:

|  | Residence Time Time (min) | Conversion (%) (acetic acid) | Conversion (%) (MeOH) | DME/MeOH ratio |
| --- | --- | --- | --- | --- |
| Run 1 | 19 | 36 | 37 | 0.003 |
| Run 2 | 75 | 36 | 36 | 0.010 |

Runs 1 and 2 demonstrate that conversion of methyl acetate and water to acetic acid and methanol does not increase with increasing reactor residence time although increased reactor residence time results in increased formation of dimethyl ether (DME), an undesirable process byproduct which must be separated from the product mixture.

EXAMPLE 4 (COMPARATIVE)

HYDROLYSIS OF METHYL ACETATE OVER AMBERLYST 131 CATALYST AT 95° C.

Amberlyst 131 ion-exchange resin (Rohm & Haas) was dried at 110° C. for 12 hours. Four grams of this resin were loaded in a reactor tube. A feed of water, methyl acetate, methanol, and acetic acid; whose mole fractions were 0.583, 0.250, 0.083, and 0.083 respectively. This feedstock represents a 25 percent hydrolyzed methyl acetate/water feedstock. The feedstock was pumped through the catalyst bed. Pressure was maintained at 150 psig and temperature was maintained at 95° C. Residence time through the bed was varied by varying the pumping rate. The bed was allowed to purge for a minimum of eight hours. Each sample was collected for a minimum of twelve hours. Samples were then analyzed by gas chromatography to determine composition. Conversion was calculated based upon acetic acid. The following results were obtained:

|       | Residence Time Time (min) | Conversion (%) (acetic acid) | Conversion (%) (MeOH) | DME/MeOH ratio |
|-------|---------------------------|------------------------------|-----------------------|----------------|
| Run 3 | 75                        | 31                           | 33                    | 0.034          |
| Run 4 | 150                       | 33                           | 31                    | 0.042          |
| Run 5 | 300                       | 33                           | 31                    | 0.075          |

Runs 3 through 5 demonstrate that conversion of methyl acetate and water to acetic acid and methanol does not increase with increasing reactor residence time although increased reactor residence time results in increased formation of dimethyl ether (DME), an undesirable process byproduct which must be separated from the product mixture.

EXAMPLE 5 (COMPARATIVE)

HYDROLYSIS OF METHYL ACETATE OVER AMBERLYST 131 CATALYST AT 150° C.

Amberlyst 131 ion-exchange resin (Rohm & Haas) was dried at 110° C. for 12 hours. Two grams of this resin were loaded in a reactor tube to form a catalyst bed. A feedstock of water, methyl acetate, methanol, and acetic acid having mole fractions 0.633, 0.300, 0.033, and 0.034 respectively. This feedstock represents a 10 percent hydrolyzed methyl acetate/water feedstock. The feedstock was pumped through the catalyst bed. Pressure was maintained at 150 psig and temperature was maintained at 150° C. Residence time through the catalyst bed was varied by varying the pumping rate. The catalyst bed was allowed to purge for a minimum of eight hours. Each sample was collected for a minimum of twelve hours. Each sample was then analyzed by gas chromatography to determine composition. Conversion was calculated based upon acetic acid and methanol. The following results were obtained:

|       | Residence Time Time (min) | Conversion (%) (acetic acid) | Conversion (%) (MeOH) | DME/MeOH ratio |
|-------|---------------------------|------------------------------|-----------------------|----------------|
| Run 6 | 10                        | 40                           | 38                    | 0.116          |
| Run 7 | 37                        | 42                           | 38                    | 0.155          |

Runs 6 and 7 demonstrate that conversion of methyl acetate and water to acetic acid and methanol does not increase with increasing reactor residence time although increased reactor residence time results in increased formation of dimethyl ether (DME), an undesirable process byproduct which must be separated from the product mixture.

EXAMPLE 6

HYDROLYSIS OF METHYL ACETATE OVER ACIDIC CARBON CATALYST AT 150° C.

Type AC Carbon (Barneby & Sutcliffe) was ground to produce a sample of 60–100 mesh size. This sample was then dried at 110° C. for 12 hours. Four grams of this acidic carbon catalyst were loaded in a reactor tube to form a catalyst bed. A feedstock of water, methyl acetate, methanol, and acetic acid having mole fractions 0.633, 0.300, 0.033, and 0.034 respectively. This feedstock represents a 10 percent hydrolyzed methyl acetate/water feedstock. The feedstock was pumped through the catalyst bed. Pressure was maintained at 200 psig and temperature was maintained at 150° C. Residence time through the catalyst bed was varied by varying the pumping rate. The catalyst bed was allowed to purge for a minimum of eight hours. Each sample was collected for a minimum of twelve hours. Each sample was then analyzed by gas chromatography to determine composition. Conversion was calculated based upon acetic acid and methanol. The following results were obtained:

|        | Residence Time Time (min) | Conversion (%) (acetic acid) | Conversion (%) (MeOH) | DME/MeOH ratio |
|--------|---------------------------|------------------------------|-----------------------|----------------|
| Run 8  | 12                        | 23                           | 22                    | 0              |
| Run 9  | 24                        | 27                           | 27                    | 0              |
| Run 10 | 48                        | 40                           | 38                    | 0              |
| Run 11 | 95                        | 42                           | 40                    | 0              |

Example 6 demonstrates that many carbon catalysts possess sufficient acidic character such that the carbon catalyst does not have be reacted with an oxidizing agent prior to conducting the claimed process. Runs 8 through 11 demonstrate that conversion of methyl acetate and water to acetic acid and methanol in the presence of Applicants' acidic carbon catalysts increases with increasing reactor residence time and increased reactor residence time does not result in formation of dimethyl ether (DME), an undesirable process byproduct which must be separated from the product mixture. This result is contrasted with the results of Examples 3 through 5 wherein increased reactor residence time did not increase conversion to products, but resulted in increasing amounts of DME being formed.

EXAMPLE 7

HYDROLYSIS OF METHYL ACETATE OVER ACIDIC CARBON CATALYST AT 150° C.

Type AC Carbon (Barneby & Sutcliffe) was ground to produce a sample of 60–100 mesh size. This sample was then dried at 110° C. for 12 hours. Four grams of this carbon were loaded in a reactor tube to form a catalyst bed. A feedstock of water, methyl acetate, methanol, and acetic acid having mole fractions 0.633, 0.300, 0.033, and 0.033 respectively. This feedstock represents a 10 percent hydrolyzed methyl acetate/water feedstock. The feedstock was pumped through the catalyst bed. Pressure was maintained at 200 psig and temperature was maintained at 150° C. Residence time through the catalyst bed was maintained at 94 minutes by maintaining a constant pumping rate. The catalyst bed was allowed to purge for a minimum of eight hours. Each sample was collected for a minimum of twelve hours per data point and was collected as a function of time on stream. Each sample was then analyzed by gas chromatography to determine composition. Conversion was calculated based upon acetic acid and methanol. The following results were obtained:

| | Time on Stream (hrs) | Conversion (%) (acetic acid) | Conversion (%) (MeOH) | DME/MeOH ratio |
|---|---|---|---|---|
| Run 12 | 192 | 41 | 40 | 0 |
| Run 13 | 312 | 42 | 40 | 0 |
| Run 14 | 408 | 41 | 40 | 0 |

Runs 12 through 14 demonstrate that catalyst activity is retained as the process is conducted over a period of time up to 408 hours. Moreover, the Runs do not yield any formation of DME thereby eliminating the need for costly separation procedures.

EXAMPLE 8

HYDROLYSIS OF METHYL ACETATE OVER ACIDIC CARBON CATALYST AT 150° C.

Type OL Carbon (Calgon) was measured and found to contain particles in the 20–35 mesh size range. This carbon was dried at 110° C. for 12 hours. Four grams of this carbon were loaded in a reactor tube to form a catalyst bed. A feedstock of water, methyl acetate, methanol, and acetic acid having mole fractions 0.567, 0.233, 0.1, and 0.1 respectively. This feedstock represents a 30 percent hydrolyzed methyl acetate/water feedstock. The feedstock was pumped through the catalyst bed. Pressure was maintained at 200 psig and temperature was maintained at 150° C. Residence time through the catalyst bed was varied by varying the pumping rate. The catalyst bed was allowed to purge for a minimum of eight hours. Each sample was collected for a minimum of twelve hours per data point. Each sample was then analyzed by gas chromatography to determine composition. Conversion was calculated based upon acetic acid and methanol. The following results were obtained:

| | Residence Time Time (min) | Conversion (%) (acetic acid) | Conversion (%) (MeOH) | DME/MeOH ratio |
|---|---|---|---|---|
| Run 15 | 13 | 39 | 37 | 0 |
| Run 16 | 26 | 38 | 37 | 0 |
| Run 17 | 52 | 40 | 39 | 0 |
| Run 18 | 104 | 40 | 39 | 0 |

EXAMPLE 9

HYDROLYSIS OF METHYL ACETATE OVER ACIDIC CARBON CATALYST AT 100° C.

Peat based Carbon was hot nitric acid treated according to the general procedure recited in Example 1. Two grams of the resulting acidic carbon catalyst were loaded into a reactor tube. A feedstock of water, methyl acetate, methanol, and acetic acid having mole fractions 0.633, 0.300, 0.033, and 0.034 respectively. This feedstock represents a 10 percent hydrolyzed methyl acetate/water feedstock. The feedstock was pumped through the catalyst bed. Pressure was maintained at 100 psig and temperature was maintained at 100° C. Residence time through the catalyst bed was varied by varying the pumping rate. The catalyst bed was allowed to purge for a minimum of eight hours. Each sample was collected for a minimum of twelve hours per data point. Each sample was then analyzed by gas chromatography to determine composition. Conversion was calculated based upon acetic acid and methanol. The following results were obtained:

| | Residence Time Time (min) | Conversion (%) (acetic acid) | Conversion (%) (MeOH) | DME/MeOH ratio |
|---|---|---|---|---|
| Run 19 | 12 | 19 | 18 | 0 |
| Run 20 | 24 | 19 | 21 | 0 |

Runs 19 and 20 illustrate that acidic carbon catalysts formed from peat which are treated with hot nitric acid are not sufficiently catalytically active to hydrolyze methyl acetate to equilibrium conversions of 36% at 100° C. However, the acidic carbon catalyst is active at 100° C., but does not reach equilibrium at the residence times tested.

EXAMPLE 10

HYDROLYSIS OF METHYL ACETATE OVER ACIDIC CARBON CATALYST AT 150° C.

A sample of peat based Carbon was treated with hot nitric acid according to the procedure of Example 1. Two grams of this carbon were loaded in a reactor tube. A feedstock of water, methyl acetate, methanol, and acetic acid having mole fractions 0.633, 0.300, 0.033, and 0.034 respectively. This feedstock represents a 10 percent hydrolyzed methyl acetate/ water feedstock. The feedstock was pumped through the catalyst bed. Pressure was maintained at 150 psig and temperature was maintained at 150° C. Residence time through the catalyst bed was varied by varying the pumping rate. The catalyst bed was allowed to purge for a minimum of eight hours. Each sample was collected for a minimum of twelve hours per data point. Each sample was then analyzed by gas chromatography to determine composition. Conversion was calculated based upon acetic acid and methanol. The following results were obtained:

| | Residence Time Time (min) | Conversion (%) (acetic acid) | Conversion (%) (MeOH) | DME/MeOH ratio |
|---|---|---|---|---|
| Run 21 | 12 | 21 | 20 | 0 |
| Run 22 | 24 | 24 | 23 | 0 |
| Run 23 | 49 | 22 | 23 | 0 |

Runs 21 through 23 illustrate that acidic carbon catalysts formed from peat which are treated with hot nitric acid are not sufficiently catalytically active to hydrolyze methyl acetate to equilibrium conversions of 42% at 150° C. However, the acidic carbon catalyst is active at 150° C., but does not reach equilibrium at the residence times tested.

EXAMPLE 11

HYDROLYSIS OF METHYL ACETATE OVER ACIDIC CARBON CATALYST AT 150° C.

A sample of Type AC Carbon (Barneby & Sutcliffe) was ground to produce a sample of 60–100 mesh size. This sample was then treated with hot $HNO_3$ and Cu(ll)acetate according to the procedure of Example 1. This sample was then dried at 110° C. for 12 hours. Four grams of this carbon were loaded in a reactor tube. A feedstock of water, methyl acetate, methanol, and acetic acid having mole fractions 0.633, 0.300, 0.033, and 0.033 respectively. This feedstock represents a 10 percent hydrolyzed methyl acetate/water feedstock. The feedstock was pumped through the catalyst bed. Pressure was maintained at 200 psig and temperature was maintained at 150° C. Residence time through the catalyst bed was maintained at 94 minutes by maintaining a constant pumping rate. The catalyst bed was allowed to purge for a minimum of eight hours. Each sample was collected for a minimum of twelve hours per data point and was collected as a function of time on stream. Each sample was then analyzed by gas chromatography to determine composition. Conversion was calculated based upon acetic acid and methanol. The following results were obtained:

|  | Time on Stream (hrs) | Conversion (%) (acetic acid) | Conversion (%) (MeOH) | DME/MeOH ratio |
| --- | --- | --- | --- | --- |
| Run 24 | 120 | 40 | 39 | 0 |
| Run 25 | 192 | 41 | 40 | 0 |
| Run 26 | 312 | 41 | 40 | 0 |
| Run 27 | 408 | 41 | 39 | 0 |

Runs 24 through 27 demonstrate that the subject acidic carbon catalysts converted a 10% hydrolyzed methyl acetate/water feedstock to 41% conversion at 150° C. at a residence time of 94 minutes.

EXAMPLE 12

HYDROLYSIS OF METHYL ACETATE OVER ACIDIC CARBON CATALYST AT 150° C.

A sample of Type OL Carbon (Calgon) was measured and found to contain particles in the 20–35 mesh size range. This carbon was washed with concentrated nitric acid by simple addition of acid to carbon in a glass beaker according to the procedure of Example 2. The carbon was rinsed with water to neutral pH and dried at 110° C. for 12 hours. Four grams of this carbon were loaded in a reactor tube. A feedstock of water, methyl acetate, methanol, and acetic acid having mole fractions 0.567, 0.233, 0.1, and 0.1 respectively. This feedstock represents a 30 percent hydrolyzed methyl acetate/water feedstock. The feedstock was pumped through the catalyst bed. Pressure was maintained at 200 psig and temperature was maintained at 150° C. Residence time through the catalyst bed was varied by varying the pumping rate. The catalyst bed was allowed to purge for a minimum of eight hours. Each sample was collected for a minimum of twelve hours per data point. Each sample was then analyzed by gas chromatography to determine composition. Conversion was calculated based upon acetic acid and methanol: The following results were obtained:

|  | Residence Time Time (min) | Conversion (%) (acetic acid) | Conversion (%) (MeOH) | DME/MeOH ratio |
| --- | --- | --- | --- | --- |
| Run 28 | 12 | 42 | 40 | 0 |
| Run 29 | 24 | 42 | 40 | 0 |
| Run 30 | 47 | 42 | 40 | 0 |

Each respective run demonstrates that the subject acidic carbon catalysts can convert a 30% hydrolyzed methyl acetate/water feed to 42% conversion at 150° C. at a residence time of 12 minutes.

EXAMPLE 13

HYDROLYSIS OF METHYL ACETATE OVER ACIDIC CARBON CATALYST AT 200° C.

A sample of Type OL Carbon (Calgon) was measured and found to contain particles in the 20–35 mesh size range. This carbon was dried at 110° C. for 12 hours. Four grams of this carbon were loaded in a reactor tube. A feedstock of water, methyl acetate, methanol, and acetic acid having mole fractions 0.567, 0.233, 0.1, and 0.1 respectively. This feedstock represents a 30 percent hydrolyzed methyl acetate/water feedstock. The feedstock was pumped through the catalyst bed. Pressure was maintained at 750 psig and temperature was maintained at 200° C. Residence time through the catalyst bed was varied by varying the pumping rate. The catalyst bed was allowed to purge for a minimum of eight hours. Each sample was collected for a minimum of twelve hours per data point. Each sample was then analyzed by gas chromatography to determine composition. Conversion was calculated based upon acetic acid and methanol. The following results were obtained:

|  | Residence Time Time (min) | Conversion (%) (acetic acid) | Conversion (%) (MeOH) | DME/MeOH ratio |
| --- | --- | --- | --- | --- |
| Run 31 | 12 | 43 | 41 | 0 |
| Run 32 | 23 | 43 | 41 | 0 |
| Run 33 | 47 | 43 | 41 | 0 |
| Run 34 | 94 | 43 | 41 | 0 |
| Run 35 | 188 | 43 | 41 | 0 |

Runs 31 through 35 demonstrate that the subject acidic carbon catalyst can convert a 30% hydrolyzed methyl acetate/water feed to 43% conversion at 200° C. at a residence time of 12 minutes.

EXAMPLE 14

HYDROLYSIS OF METHYL ACETATE OVER ACIDIC CARBON CATALYST AT 200° C.

A sample of Type OL Carbon (Calgon) was measured and found to contain particles in the 20–35 mesh size range. This carbon was washed with concentrated nitric acid by simple addition of acid to carbon in a glass beaker according to the procedure of Example 2. The carbon was rinsed with water to neutral pH and dried at 110° C. for 12 hours. Four grams of this carbon were loaded in a reactor tube. A feedstock of water, methyl acetate, methanol, and acetic acid having mole fractions 0.633, 0.300, 0.033, and 0.033 respectively. This feedstock represents a 10 percent hydrolyzed methyl acetate/water feedstock. The feedstock was pumped through the catalyst bed. Pressure was maintained at 750 psig and temperature was maintained at 200° C. Residence time through the catalyst bed was varied by varying the pumping rate. The catalyst bed was allowed to purge for a minimum of eight hours. Each sample was collected for a minimum of twelve hours per data point. Each sample was then analyzed by gas chromatography to determine composition. Conversion was calculated based upon acetic acid and methanol. The following results were obtained:

|  | Residence Time Time (min) | Conversion (%) (acetic acid) | Conversion (%) (MeOH) | DME/MeOH ratio |
|---|---|---|---|---|
| Run 36 | 12 | 40 | 38 | 0 |
| Run 37 | 23 | 41 | 39 | 0 |
| Run 38 | 47 | 43 | 41 | 0 |
| Run 39 | 94 | 43 | 41 | 0 |

Runs 36 through 39 demonstrate that the subject acidic carbon catalyst is capable of converting a 10% hydrolyzed methyl acetate/water feed to 43% conversion at 200° C. at a residence time of 47 minutes.

The process according to the claimed invention provides hydrolysis catalysts that can operate at high temperatures in order to maximize conversion of carboxylic acid alkyl esters to the desired products of the corresponding carboxylic acid and alcohol while minimizing formation of undesirable byproducts such as dialkyl ethers which are difficult to separate from the product mixture.

We claim:

1. A liquid-phase process for hydrolyzing a carboxylic acid alkyl ester having 2 to 18 carbon atoms to provide a product mixture comprising a carboxylic acid and an alcohol comprising contacting a feedstock comprising the carboxylic acid alkyl ester and water with an acidic carbon catalyst under reaction conditions sufficient to form the product mixture comprising the carboxylic acid and the alcohol.

2. The liquid-phase process according to claim 1 wherein the acidic carbon catalyst is formed by contacting a carbon catalyst with nitric acid prior to conducting the process.

3. The liquid-phase process according to claim 1 wherein the reaction conditions comprise a temperature ranging from 40° to 200° C.

4. The process according to claim 1 wherein the carboxylic acid alkyl ester is represented by the formula $RCO_2R'$ wherein R represents a hydrogen atom, a linear or branched alkyl having from 1 to 16 carbon atoms, phenyl, naphthyl, alkyl-substituted phenyl or alkyl-substituted naphthyl and R' represents a linear or branched alkyl having from 1 to 17 carbon atoms, phenyl, naphthyl, alkyl-substituted phenyl or alkyl-substituted naphthyl.

5. The process according to claim 4 wherein the product mixture comprises an alcohol represented by the formula R'—OH and a carboxylic acid represented by the formula $RCO_2H$ wherein R' and R are as defined above in claim 4.

6. The process according to claim 5 further comprising separating the carboxylic acid from the product mixture.

7. The process according to claim 5 further comprising separating the alcohol from the product mixture.

8. A liquid-phase process for hydrolyzing a carboxylic acid methyl ester represented by the formula $RCO_2CH_3$ wherein R represents a hydrogen atom or a linear or branched alkyl having from 1 to 16 carbon atoms to provide a product mixture comprising a carboxylic acid and methanol comprising contacting a feedstock comprising the carboxylic acid methyl ester and water with an acidic carbon catalyst under reaction conditions sufficient to provide the product mixture comprising the carboxylic acid and methanol.

9. The liquid-phase process according to claim 8 wherein the acidic carbon catalyst is formed by contacting a carbon catalyst with nitric acid prior to conducting the process.

10. The liquid-phase process according to claim 8 wherein the reaction conditions comprise a temperature ranging from 60° to 200° C.

11. The process according to claim 8 wherein the product mixture comprises a carboxylic acid represented by the formula $RCO_2H$ wherein R is as defined above in claim 8.

12. The process according to claim 8 wherein the carboxylic acid methyl ester is methyl acetate, the carboxylic acid is acetic acid and the alcohol is methanol.

13. The process according to claim 12 wherein the reactions conditions comprise a temperature ranging from 60° to 200° C.

* * * * *